(12) United States Patent
Carl

(10) Patent No.: US 6,978,689 B2
(45) Date of Patent: Dec. 27, 2005

(54) DISPENSING APPARATUS HAVING MEANS FOR LOADING PIPETTE TIPS IN A DISPENSE HEAD

(75) Inventor: Richard A. Carl, Rancho Pales Verdes, CA (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 10/941,773

(22) Filed: Sep. 15, 2004

(65) Prior Publication Data

US 2005/0178217 A1 Aug. 18, 2005

Related U.S. Application Data

(63) Continuation of application No. 10/464,426, filed on Jun. 18, 2003, now Pat. No. 6,810,757, which is a continuation of application No. 10/027,448, filed on Dec. 20, 2001, now Pat. No. 6,622,578, which is a continuation of application No. 09/442,500, filed on Nov. 18, 1999, now Pat. No. 6,415,669, which is a continuation-in-part of application No. 09/056,880, filed on Apr. 9, 1998, now abandoned.

(51) Int. Cl.[7] .............................................. G01N 1/00
(52) U.S. Cl. ................................................. 73/864.14
(58) Field of Search ................... 73/863.32, 864.01, 73/864.14, 864.16, 864.17; 422/100, 104

(56) References Cited

U.S. PATENT DOCUMENTS

| | | | |
|---|---|---|---|
| 4,284,604 A | 8/1981 | Tervamäki | 422/100 |
| 4,532,805 A | 8/1985 | Flesher | 73/863.32 |
| 4,565,100 A | 1/1986 | Malinoff | 73/863.32 |
| 4,933,291 A | 6/1990 | Daiss et al. | 436/45 |
| 5,061,449 A | 10/1991 | Torti et al. | 422/100 |
| 5,232,669 A | 8/1993 | Pardinas | 422/100 |
| 5,343,909 A | 9/1994 | Goodman | 141/242 |
| 5,497,670 A | 3/1996 | Carl | 73/863.32 |
| 5,507,193 A | 4/1996 | Ishihara | 73/864.24 |
| 5,736,105 A | 4/1998 | Astle | 422/100 |
| 5,915,284 A | 6/1999 | Meltzer et al. | 73/864.17 |
| 6,143,252 A * | 11/2000 | Haxo et al. | 422/131 |
| 6,622,578 B2 | 9/2003 | Carl | 73/864.14 |

FOREIGN PATENT DOCUMENTS

| | | |
|---|---|---|
| DE | 3921 729 A1 | 1/1991 |
| EP | 0 747 125 A2 | 12/1996 |
| FI | 41466 | 7/1969 |

* cited by examiner

Primary Examiner—Robert Raevis
(74) Attorney, Agent, or Firm—Seed IP Law Group PLLC

(57) ABSTRACT

A self contained dispensing head apparatus wherein a modified pipette tip box tray carrier is utilized to furnish pipette tips, carried in a standard pipette tip box, by a pipette tip box tray carrier to the head apparatus and wherein means are provided to engage the pipette tip box tray carrier in a manner whereby the pipette tips are loaded into corresponding internal cylinders formed in the dispense block head. The dispense block head comprises a solid block of material having a plurality of internal cylinders to engage the pipette tips in a sealing arrangement. The pipette tips are modified from the conventional design in that a disk-shaped ring portion is interposed adjacent one end of the pipette tip, a tapered end of the tip allowing a seal to be formed with the dispense block head internal cylinders.

8 Claims, 7 Drawing Sheets

DISPENSING APPARATUS HAVING MEANS FOR LOADING PIPETTE TIPS IN A DISPENSE HEAD

CROSS-REFERENCE TO RELATED APPLICATIONS

This is a continuation of application Ser. No. 10/464,426, filed Jun. 18, 2003 now U.S. Pat. No. 6,810,757, which is a continuation of Ser. No. 10/027,448, filed Dec. 20, 2001, issued on Sep. 23, 2003 as U.S. Pat. No. 6,622,578, which is a continuation application of application Ser. No. 09/442,500, filed Nov. 18, 1999, issued on Jul. 9, 2002 as U.S. Pat. No. 6,415,669, which is a continuation-in-part of application Ser. No. 09/056,880, filed Apr. 9, 1998, which has abandoned.

BACKGROUND OF THE INVENTION

1. Field of the Invention

The present invention provides apparatus for aspirating and dispensing controlled amounts of liquid from a solid dispense block into receptacles, the apparatus including means for loading pipette tips designed for sealing on its outside diameter into internal cylinders within the dispense block head.

2. Description of the Related Art

U.S. Pat. No. 5,497,670 issued Mar. 12, 1996, the subject matter set forth therein invented by the inventor of the present invention, discloses an improved dispensing head apparatus including means for loading pipette tips carried by a pipette plate onto dispensing cylinders, the loading force being maintained during the apparatus operation cycle, thus ensuring a hermetic seal. The pipette tips are manually placed on the tip plate, the plate sliding within the dispensing apparatus.

Although the pipette tip plate holder described in the aforementioned patent provides many advantages when used with the apparatus described therein, there are certain disadvantages associated with its use. In particular, there is a possibility that the pipette tip slide plate may become contaminated. Most importantly, the pipette tip plate configuration is not easily adapted for robotics operation or automation.

U.S. patent application Ser. No. 08/751,859 filed Nov. 18, 1996, the subject matter set forth therein also invented by the inventor of the present invention, provides a self contained head dispensing apparatus similar to that disclosed in the aforementioned patent but modified to the extent that the pipette tip plate disclosed therein is replaced with a more conventional pipette tip carrier which is less expensive, is less likely to be contaminated and wherein the carrier is easily adapted for robotics operation or automation.

A microplate typically holding 96 wells with 9 mm on centers spacing in a 8 by 12 array is typically used with most dispense apparatus. The early prior art dispense devices started with one dispenser and moved in the X-Y direction 96 times to dispense into each of the 96 wells. Over time, dispense devices were added to include one row (8 or 12 wells per row) and then indexing either 8 or 12 times to fill the entire plate. A 96 dispense apparatus device to fill an entire plate at one time is disclosed, for example, in the '670 patent noted above.

The microplate has recently changed in design. Higher production speeds and larger storage libraries required higher density formats. The 96 well format with its 9 mm spacing has increased to 384 with 4.5 mm spacing. The 384 microplate has increased to 864 and now 1536 with 2.25 mm spacing. These different density plates have the same foot print (length, width).

In the dispensing method disclosed in the '859 application, a pipette that fits on the outside of a cylinder and tapers down to a small point is used. Most pipette dispensing systems are connected to the cylinder used in the dispensing head using an "O" ring to ensure a proper fluid seal from the pipette inside diameter ("ID") to the cylinders outside diameter ("OD"). The typical pipette seals on its ID and therefore builds up the OD of the pipette. The typical OD is larger than 4.5 mm and therefore makes it difficult for use with higher density formats dispensing like 384 (4.5 mm spacing) since the 384 microplate has 4.5 mm spacing—therefore a pipette is to be used on the 384 format must have an OD that is smaller than 4.5 mm.

Prior art dispense devices, like the one disclosed in the '679 patent, use separate cylinders (one for each pipette), 96 total. This is the easiest way to connect to the pipettes ID. If a pipette is designed that seals on its OD, a new dispense head design is required. This would include sealing, loading, and stripping methods.

What is thus desired is to provide a new pipette design that allows sealing on its outside diameter with means of loading and stripping and to provide a new dispense apparatus that essentially comprises an integral solid block and which does not require discrete cylinders.

BRIEF SUMMARY OF THE INVENTION

The present invention provides a self contained dispensing head apparatus wherein a pipette tip box tray carrier is utilized to furnish pipette tips, carried in a standard pipette tip box, to the head apparatus and wherein means are provided to engage the tray carrier in a manner whereby the pipette tips are loaded in corresponding internal cylinders (openings) in the apparatus. The dispense block head comprises a solid block of material having a plurality of internal cylinders to engage the pipette tips in a sealing arrangement.

The pipette tips are modified from the conventional design in that a disk-shaped ring portion is interposed adjacent to one end of the pipette, the upper tapered portion allowing the dispense head internal cylinders to form a seal therewith.

The present invention thus provides a dispensing head apparatus which enables liquid to be aspirated from a first microplate and dispensed into a second microplate using various array formats, the dispense block head being formed from one solid block, thus substantially reducing manufacturing costs. The dispense head also allows a tight array of internal cylinders to be provided thus accommodating higher density format microplates.

BRIEF DESCRIPTION OF THE SEVERAL VIEWS OF THE DRAWINGS

For a better understanding of the invention as well as other objects and further features thereof, reference is made to the following description which is to be read in conjunction with the accompanying drawing wherein.

DETAILED DESCRIPTION OF THE INVENTION

The basic liquid dispensing apparatus and in particular, the apparatus used to move the various components, such as the tip box tray carrier 22, are described in U.S. patent application Ser. No. 08/751,859, filed Nov. 18, 1996, and will not be repeated herein for the sake of brevity. The discussion that follows will be directed to the new pipette tip design and the dispense head apparatus, both together allowing a 384 microplate (and multiples thereof) to be used for receiving and dispensing liquids.

The present invention is directed to a new pipette tip that is able to seal on the outside diameter (OD) and capable of automatic tip loading and stripping (unloading). In addition, the dispense head apparatus incorporates a new pipette dispense block head capable of dispensing or aspirating fluid at one time into a 384 microplate or, with multiple motions, into a 1536 microplate. A motion plate, not the subject of the present invention, can be used to index for 96 to 384 or 384 to 1536 microplate replication of transfer. The dispense block head is fabricated from a solid block rather than 384 separate cylinders as would be required by the design set forth in application Ser. No. 08/751,859 and thus, functions, in essence, as a cylinder head.

Figure 1:
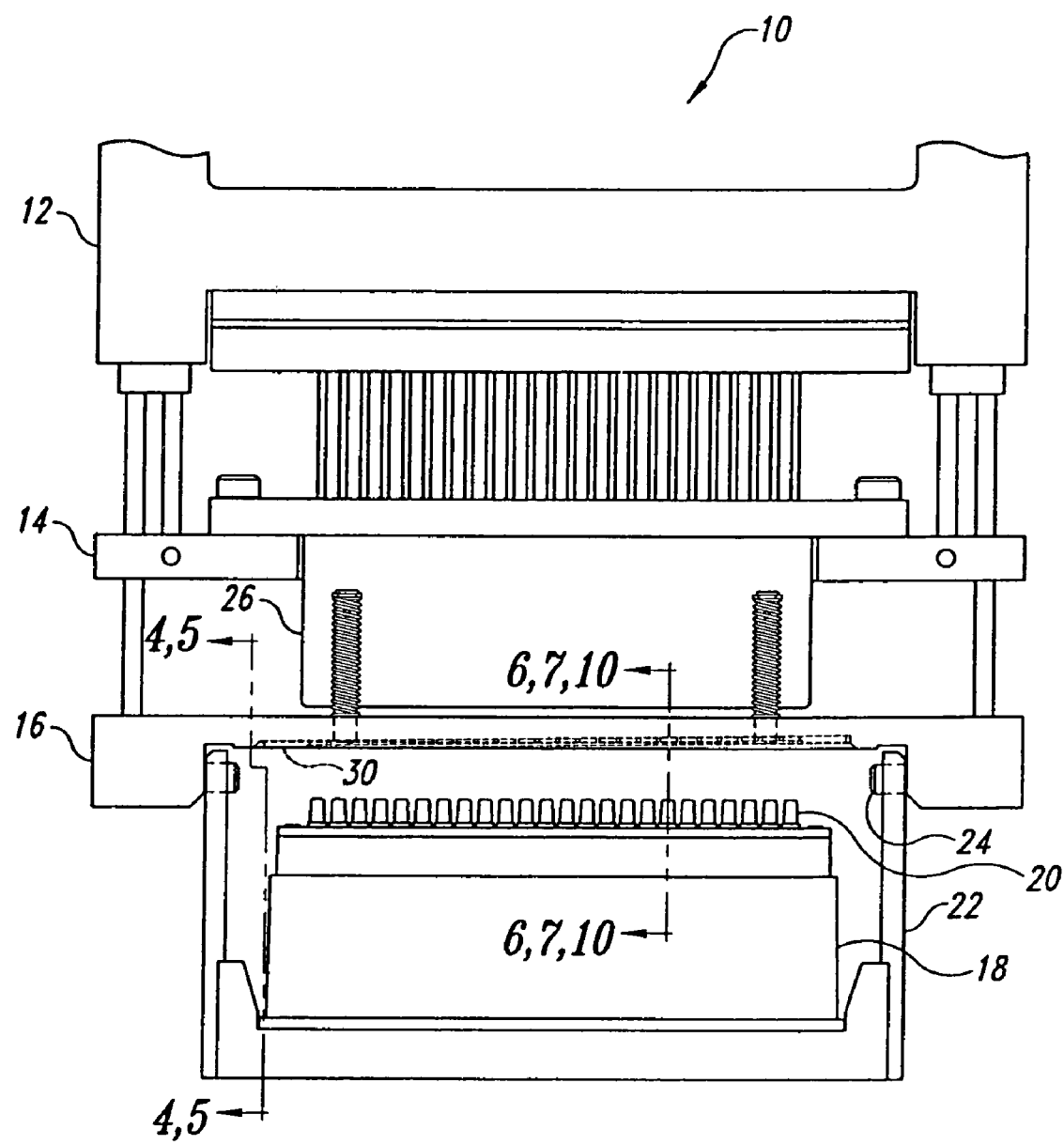
FIG. 1 is a side view of the dispense head apparatus with a pipette tip box to be loaded from the pipette tip box tray carrier.
Figure 3:
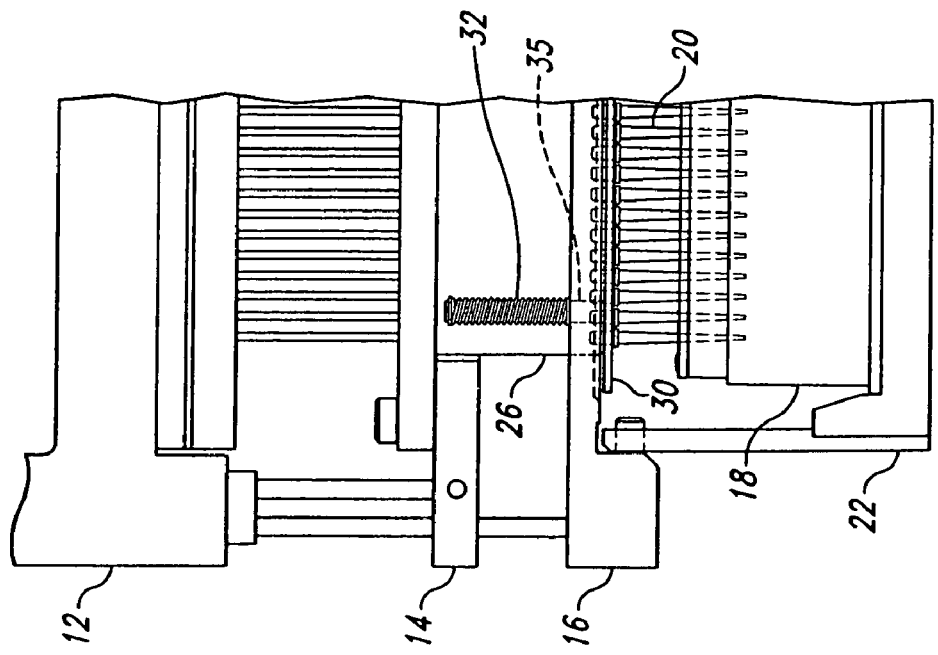
FIG. 3 illustrates the removal of the pipette tips from the pipette tip box.

FIG. 1 is a simplified front view of the dispense head apparatus 10 of the present invention. The dispense head apparatus 10 is basically identical to the apparatus described in the '859 application except for the new dispense block head 26 and pipette tip 20. In particular, dispense head apparatus 10 comprises piston plate 12, horseshoe plate 14, movable pipette tip box carrier loading plate 16, 384 pipette tip box 18, pipette tips 20, pipette tip box tray carrier 22, pipette tip box tray carrier loading pins 24 and dispense block head 26. A floating stripper plate 30, described in more detail hereinafter, is also new to dispense head apparatus 10.

Figure 2:
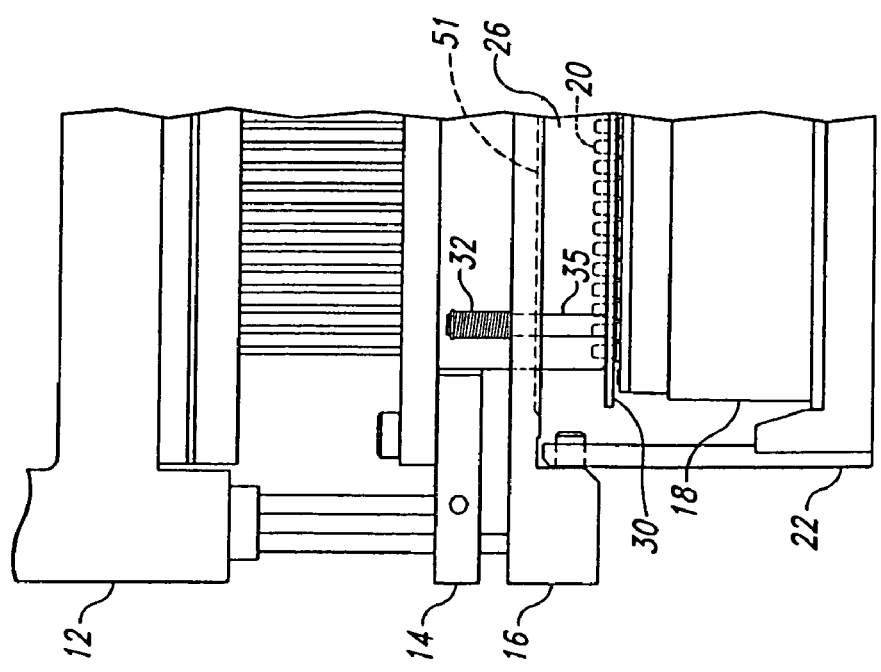
FIG. 2 illustrates loading of pipette tips to the dispense head block.
Figure 6:
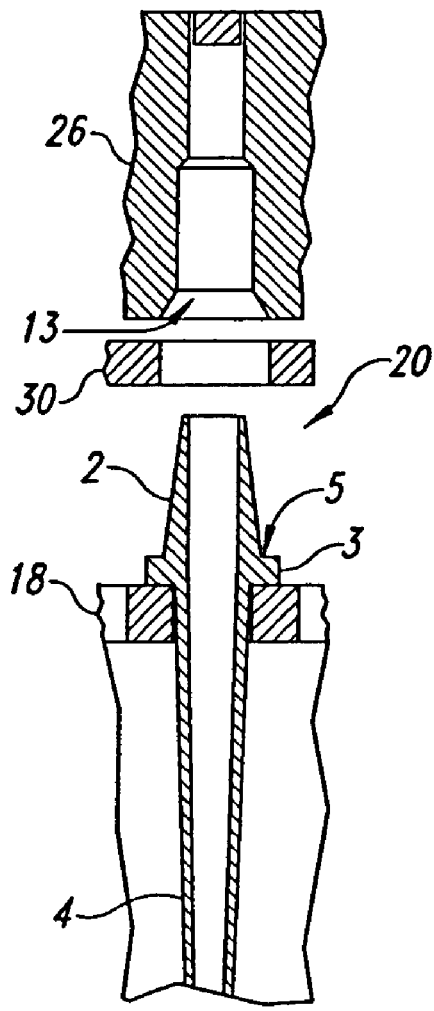
FIG. 6 is an enlarged partial cross-sectional view of the dispense block head and a pipette tip positioned for sealing engagement.
Figure 7:
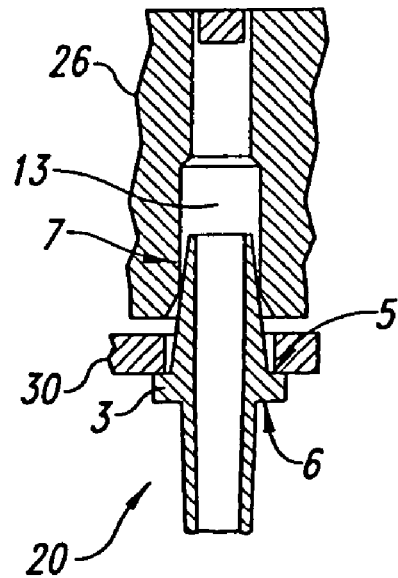
FIG. 7 illustrates the pipette tip of FIG. 6 engaged in the dispense block head.

FIGS. 6 and 7 illustrate the upper tapered portion 2 of pipette tip 20 which is positioned to be loaded with the dispense block head 26 shown in FIG. 1. Pipette tip 20, formed of plastic material, comprises upper tapered portion 2 adapted to form a sealing interface 7 as shown in FIG. 7 when loaded into the dispense block head 26. The upper tapered portion 2 also functions to center the pipette tip 20 into the internal cylinder 13 formed in dispense block head 26 (in the figure illustrated, dispense block head 26 comprises 384 internal cylinders; only one internal cylinder of the 384 holes is illustrated) during tip loading as shown in FIG. 2. The centering function of upper tapered portion 2 also accommodates for pipette tip variations that normally occur in the molding process while still providing a useable hermetic seal for the 384 pipette tips used (the number of pipette tips used correspond to the number of internal cylinders in dispense block head 26). A disk-shaped ring portion 3 separates the upper tapered portion 2 from lower tapered portion 4, the disk-shaped ring portion 3 having an upper surface 5 and lower surface 6. During the tip loading sequence, lower surface 6 of disk-shaped ring portion 3 rests on the pipette tip box 18 and when the pipette tip box 18 is pulled up during the loading sequence (similar to the process in the aforementioned patent application), the pipette tips 20 are pneumatically forced into the dispense block head 26 to create a hermetic seal with upper tapered portion 2 and internal cylinder 13. The axial loading force displaces the pipette tip 20 to ensure that the seal is made with the outside diameter of the upper tapered portion of the internal cylinder 13 and is frictionally held captive during aspirating and dispensing.

As illustrated in FIG. 6, the internal bore extends along the length of the pipette tip 20. This shape is preferred because, as discussed herein, the pipette tip 20 is designed for precisely measuring fluids, and it distinguishes a measuring pipette tip from other types of pipette tips, such as centrifugable pipette tips. As generally understood in the art, a centrifugable pipette tip to function properly has a substantially tapered bore (i.e., tapered 20 degrees or more), and has multiple chambers for retaining the separated solids.

As illustrated in FIG. 6, and as readily appreciated geometrically, the bore is numerous orders of magnitude longer than it is in diameter.

Figure 4:
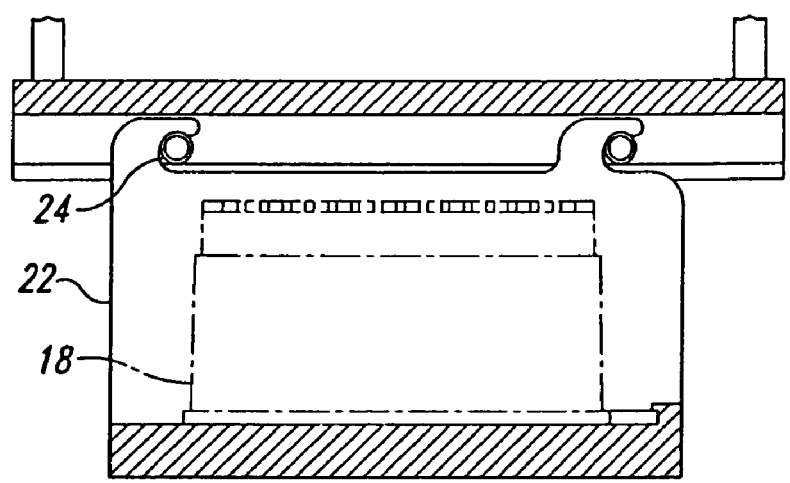
FIG. 4 is a sectional view of the tray carrier engaged with the tip box tray carrier loading plate.
Figure 5:
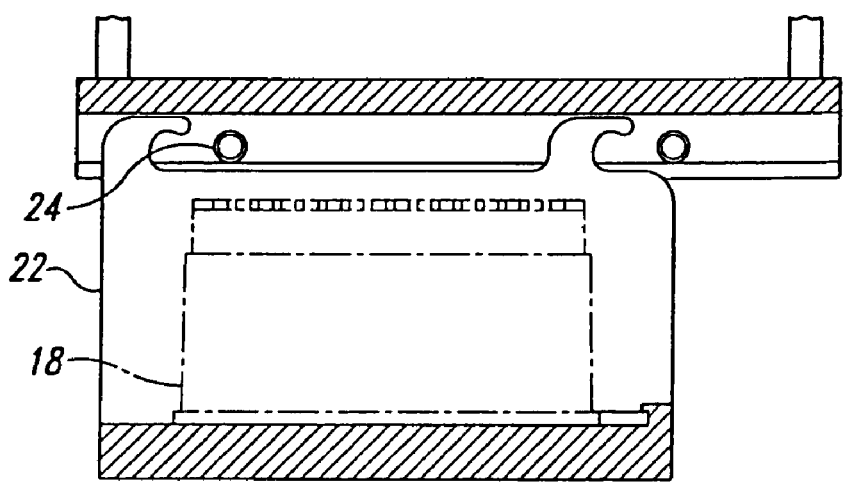
FIG. 5 illustrates the tray carrier of FIG. 4 with the pipette tip box being removed from the tip box tray carrier loading plate.

The pipette tip loading sequence transfers pipette tips 20 from the pipette tip box 18 and with an upward force axially loads them into the dispensing block head 26 as shown. The mechanical method of loading the pipette tip 20 by moving the dispense block head 26 in x, y, z motions is the same as set forth in the aforementioned application with the addition of a floating stripper plate 30 incorporated into the dispense head apparatus 10. As the loading sequence begins, the movable pipette tip box tray carrier loading plate 16, with alignment provided by floating stripper plate guide pins 35, raises (pulling with it) pipette tip box tray carrier 22, and pipette tip box 18 with pipette tip 20, up toward the dispense block head 26 to mate, compressing floating stripping plate return springs 32 against movable pipette tip box tray carrier loading plate 16. This allows the free passage of the dispense block head 26 through the movable pipette tip box tray carrier loading plate 16 while at the same time creating a zero gap condition between the floating stripper plate 30 and the dispense block head 26. The pipette tip box 18 continues upward, pushing the pipette tips 20 by applying force to the lower surface 6 of disk-shaped ring portion 3, into the dispensing block head 26 and its sealing interface 7 as shown in FIG. 7. Floating stripper plate 30 is now positioned between dispense block head 26 and the disk-shaped ring portion 3. The pipette tip 20 is now seated and hermetically sealed within the internal cylinders 13 in dispense block head 26. FIG. 4 illustrates the pipette tip box tray carrier 22 engaged with tip box tray carrier loading plate 16 therefor. FIG. 5 illustrates the pipette tip box tray carrier 22 with pipette tip box 18 being disengaged from the movable pipette tip box tray carrier loading plate 16. The dispense block head 26 is now free to travel. When the pipette tips 20 are to be stripped, the opposite sequence is performed in the manner set forth in the aforementioned application.

In order to strip the pipette tips 20 from the dispense block head 26, the following sequence occurs:

1. The dispense block head 26 is in a fixed position and the movable pipette tip box tray carrier loading plate 16 moves down (dispense block head 26 in essence, functions as a cylinder block).

2. The movable pipette tip box carrier loading plate 16 has an inclined surface pocket 51 at its bottom surface; inclined surface pocket 51 mates with the floating stripper plate 30 causing the floating stripper plate 30 to also be inclined in the downward movement. The floating stripper plate alignment pins 32 pass through a tapered hole in the movable pipette tip box tray carrier loading plate 16. The taper allows the floating stripper plate 30 to conform to the inclined surface pocket 51 of movable pipette tip box tray carrier loading plate 16.

3. The continuing downward motion of the floating stripper plate 30 eventually contacts the upper surface 5 of disk-shaped ring portion 3.

Figure 9:
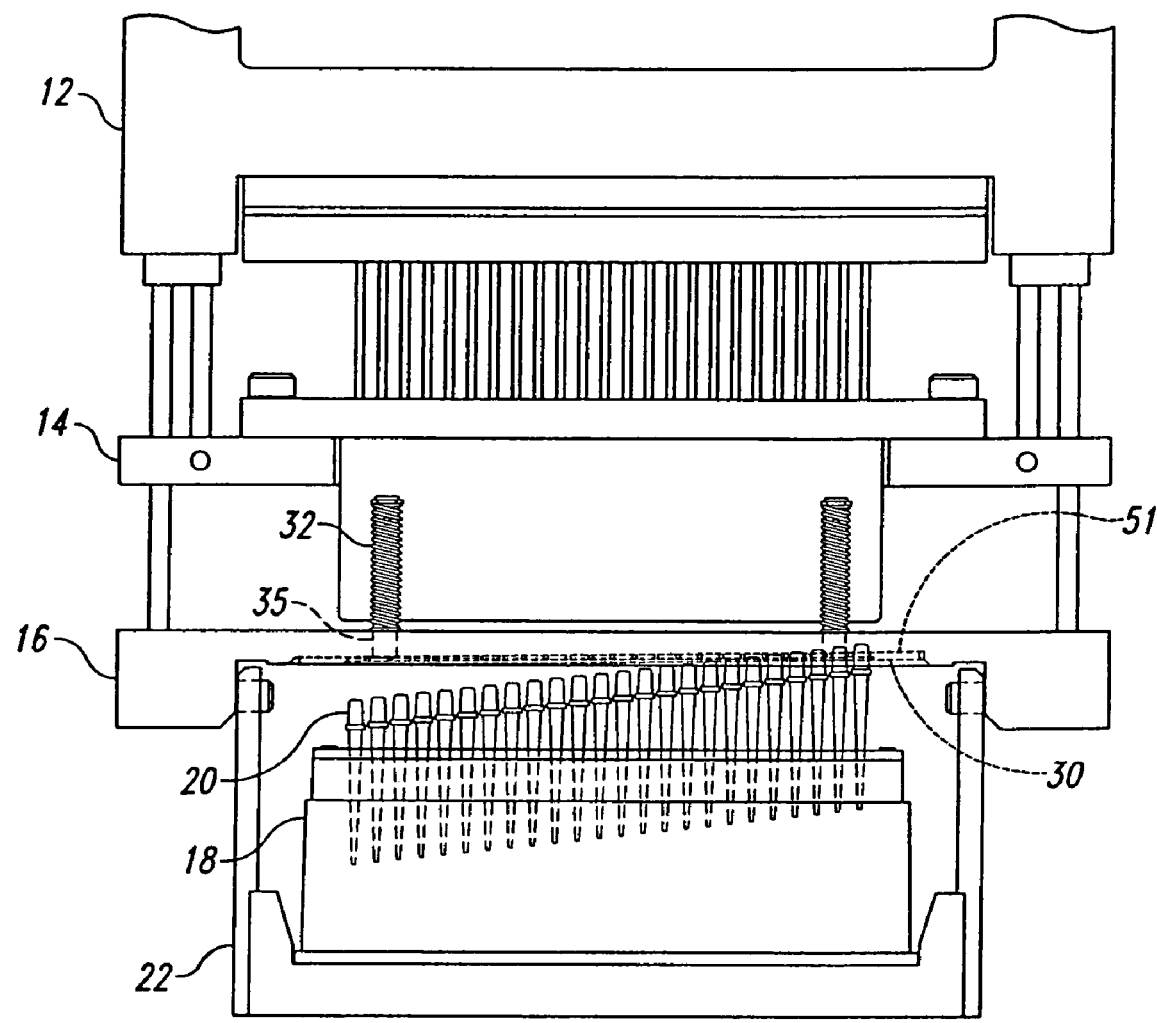
FIG. 9 is a side view of the dispense head apparatus illustrating the dispense head apparatus stripping pipette tips back into the pipette tip box.
Figure 10A:
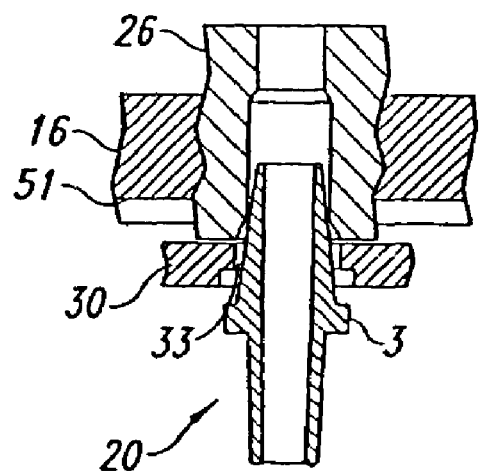
FIGS. 10A and 10B illustrate the stages in stripping a single pipette tip from the dispense head apparatus.
Figure 10B:
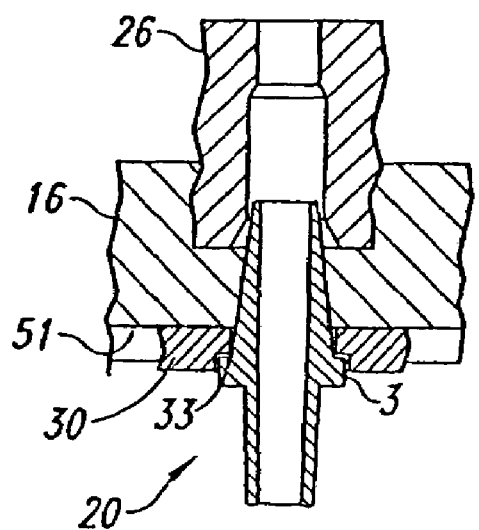

4. Since the dispense block head 26 is in a fixed position, the motion of movable pipette tray carrier loading plate 16 and floating stripper plate 30 causes pipette tips 20 to be stripped in a sequential manner. FIG. 9 illustrates the floating stripper plate 30 and movable pipette tip box carrier loading plate 16 engaged and fully extended, and stripping pipette tips 20 from dispense block head 26. FIGS. 10A and 10B illustrate two stages in the ejection of a single pipette tip 20 from the dispense block head 26. In FIG. 10A, the movable tip box pipette carrier loading plate 16 is moving downwards towards floating stripper plate 30; in FIG. 10B, movable pipette tip box carrier plate 16 is in engagement with floating stripper plate 30. A counterbore 33 is formed in floating stripper plate 30 to allow the disk-shaped ring portion 3 of pipette tips 20 to be seated therein when loaded into dispense block head 26 and, in turn, to be stripped by floating stripper plate 30.

The inclined pocket 51 assures smooth operation by not forcing all of the pipette tips 20 from the dispense block head 26 at one time, allowing instead stripping of the tips one row at a time. The stripping function is provided by an axial force applied to the top surface 5 of disk-shaped ring portion 3 on the pipette tip 20 until all have fallen into pipette tip box 18. Once the pipette tips 20 are loaded back into the pipette tip box 18, the pipette tip box 18 and pipette tip box tray carrier 22 are lowered to a table using dispense head apparatus 10 "X", "Y", "Z" motions.

Figure 8:
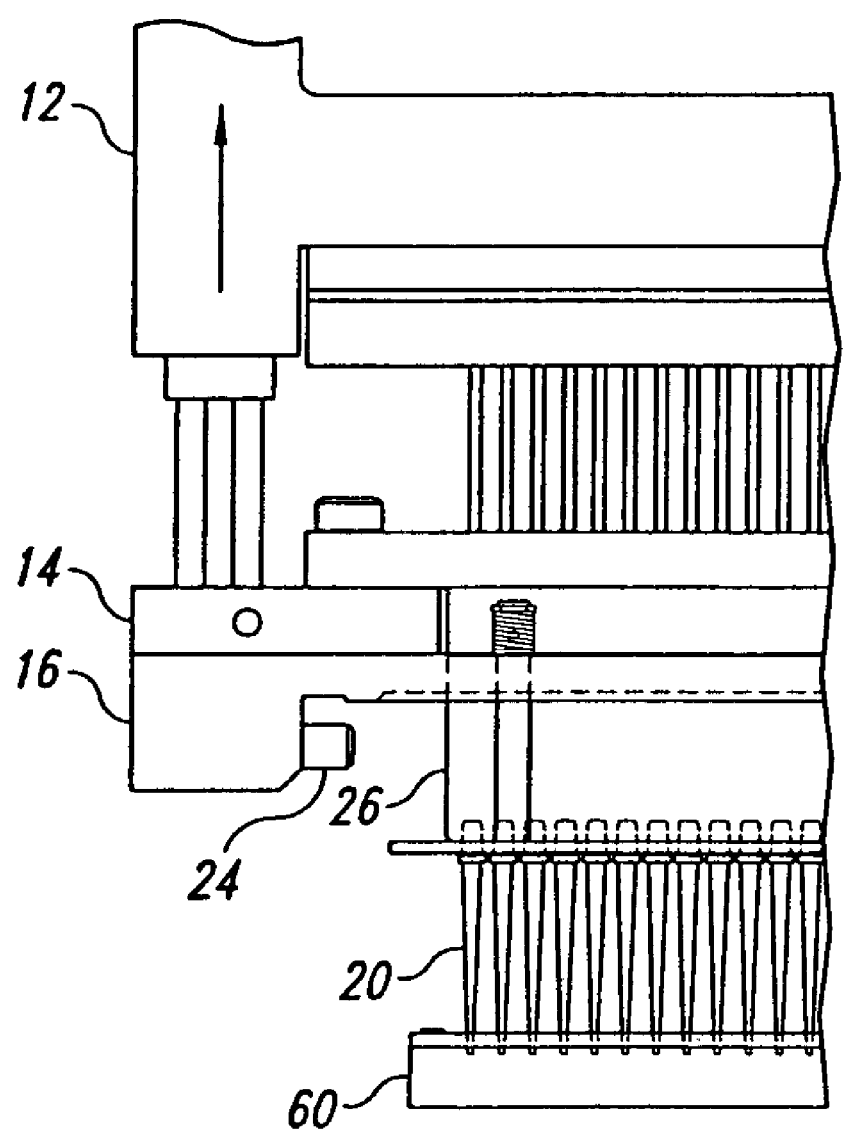
FIG. 8 illustrates the dispense head apparatus aspirating from a 384 well microplate.

FIG. 8 illustrates the dispense apparatus being used to aspirate from a 384 microplate 60.

The present invention thus provides an improved dispense head and associated pipette tips which is usable with the higher density microplates now available and wherein the manufacturing cost of the dispense head is substantially reduced.

While the invention has been described with a reference to its preferred embodiment, it will be understood by those skilled in the art that various changes may be made and equivalents may be substituted for elements thereof without departing from the true spirit and scope of the invention. In addition, modifications may be made to adapt a particular situation or material to the teachings of the invention without departing from its essential teachings.

What is claimed is:

1. A system for simultaneously dispensing precise amounts of fluid into numerous receptacles, the system comprising:

a head having a plurality of cylinders internal to the head extending at least substantially parallel to each other from an upper surface of the head to a lower surface of the head, each cylinder being configured to receive a plunger and to allow the plunger to move axially within the cylinder, each cylinder terminating at the lower surface of the head in a mouth;

a plurality of pipette tips removably engaged with the head, each tip at least partially penetrating one of the cylinders in the head and sealingly engaging the corresponding mouth; and a stripping plate positioned between the head and a raised central portion of each of the pipette tips, the stripping plate having a plurality of holes therein, each hole being large enough to allow an upper portion of the corresponding pipette tip to pass therethrough unobstructed but being too small to allow the respective raised central portion to pass therethrough such that movement of the stripping plate away from the head will urge the pipette tips out of the head, the stripping plate being oriented at an angle with respect to the lower surface of the head such that the pipette tips will be removed from the head a few at a time as the stripping plate moves away from the head.

2. The system of claim 1 wherein the head is of unitary construction.

3. The system of claim 1 wherein the plurality of cylinders comprises at least 384 cylinders arranged in an array.

4. The system of claim 1 wherein the cylinders arranged in an array in which a centerline of each cylinder is approximately 4.5 millimeters from the centerline of the adjacent cylinders.

5. The system of claim 1 wherein the mouth of each cylinder has a substantially cylindrical upper portion and a substantially frustum-shaped lower portion.

6. The system of claim 1 wherein the upper portion of each pipette tip is frustum-shaped.

7. The system of claim 1 wherein the mouth of each cylinder has a substantially cylindrical upper portion and a substantially frustum-shaped lower portion and wherein the upper portion of each pipette tip is frustum-shaped, the lower portion of the mouth having a smaller angle than the upper portion of the pipette tip with respect to the lower surface of the head such that a contact surface between the pipette tip and the head is in the shape of a circle.

8. A system for using disposable pipette tips to simultaneously dispense a precise amount of fluid into at least 384 receptacles, the system comprising:

a head having at least 384 cylinders therein extending substantially parallel to each other from an upper surface of the head to a lower surface of the head, each cylinder being configured to sealingly receive a plunger and to allow the plunger to move axially within the cylinder, each cylinder terminating at the lower surface of the head in a mouth;

a respective plurality of pipette tips housed in a pipette tip box, each pipette tip having an upper portion separated by a raised central portion from a lower portion, the raised central portion of the pipette tip being supported by the box such that urging the pipette tip box against the head results in loading the pipette tips onto the head, the upper portion of each tip being sized to at least partially penetrate one of the cylinders in the head and sealingly engage the corresponding mouth; and a stripping plate positioned adjacent the head, the stripping plate having a plurality of holes therein, each hole being large enough to allow the upper portion of the corresponding pipette tip to pass therethrough unobstructed for engagement with the head, but being too small to allow the respective raised central portion to pass therethrough such that movement of the stripping plate away from the head will urge the pipette tips out of the head.

* * * * *